United States Patent [19]

Fujii et al.

[11] 4,214,093
[45] Jul. 22, 1980

[54] AMINO- OR GUANIDINO-1,2,3,4-TETRAHYDRO-1-NAPHTHOIC ESTERS

[75] Inventors: Setsuro Fujii, Toyonaka; Yojiro Sakurai, Kamakura; Toyoo Nakayama; Ryoji Matsui, both of Funabashi, all of Japan

[73] Assignee: Torii & Co., Ltd., Tokyo, Japan

[21] Appl. No.: 30,594

[22] Filed: Apr. 16, 1979

Related U.S. Application Data

[63] Continuation-in-part of Ser. No. 953,735, Oct. 23, 1978, abandoned.

[30] Foreign Application Priority Data

Oct. 27, 1977 [JP] Japan .................. 52-128874
Oct. 27, 1977 [JP] Japan .................. 52-128875

[51] Int. Cl.² .................. C07C 101/48; A61K 31/24
[52] U.S. Cl. .................. 560/34; 260/465 D; 424/309; 560/21; 560/45; 560/48
[58] Field of Search .................. 560/34, 45, 21, 48; 260/465 D

[56] References Cited

FOREIGN PATENT DOCUMENTS 1905813 3/1970 Fed. Rep. of Germany ........... 560/34

OTHER PUBLICATIONS

Sergievskaya et al., Chem. Absts., 47, 8053(d), 1953.
Hohenlohe—Oehringen, Chem. Absts., 53, 7110(f), 1959.

*Primary Examiner*—G. T. Breitenstein
*Attorney, Agent, or Firm*—Beveridge, DeGrandi, Kline & Lunsford

[57] ABSTRACT

Amino- or guanidino-1,2,3,4-tetrahydro-1-naphthoic esters represented by the formula,

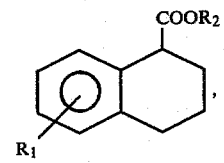

wherein $R_1$ is —NH₂ or

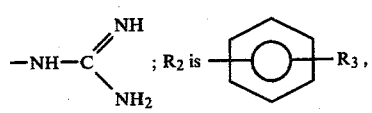

; $R_2$ is

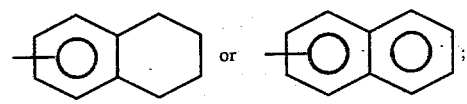

$R_3$ is —H, —$R_4$, —O—$R_4$, —NHCOCH₃, a halogen, —CN,

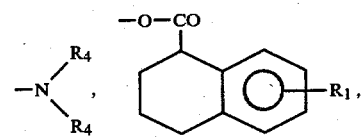

—COOH, —COOR₄,

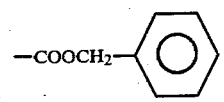

or —(CH₂)$_n$—COOCH₂—CO—R₅; R₅ is —O—R₄, —NH₂ or

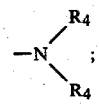

n is 0, 1 or 2, and $R_4$ is a lower alkyl, or pharmaceutically acceptable acid addition salts thereof. Owing to their inhibitory activity on proteolytic enzymes the said esters and acid addition salts thereof are useful in the therapy of diseases caused by such enzymes.

12 Claims, No Drawings

AMINO- OR GUANIDINO-1,2,3,4-TETRAHYDRO-1-NAPHTHOIC ESTERS

CROSS-REFERENCES TO RELATED APPLICATIONS

This is a continuation-in-part of copending application Ser. No. 953,735 filed Oct. 23, 1978, now abandoned, the contents of which are hereby incorporated by reference.

This invention relates to novel amino- or guanidino-1,2,3,4-tetrahydro-1-naphthoic esters or pharmaceutically acceptable acid addition salts thereof, which show an inhibitory activity on proteolytic enzymes.

Although ethyl 5- or 7-amino-1,2,3,4-tetrahydro-1-naphthoate is a known compound as described in S. I. Sergievskaya and N. P. Volgnskii, Zhur. Obshchei Khim. (J. Gen. Chem.), 22, 1035 (1952) [C. A. 47 8053a (1953)], no suggestion can be found in the literature whether or not this ester exhibits an inhibitory activity on proteolytic enzymes.

The present inventors have conducted studies on novel compounds having an enzyme-inhibitory activity and, as a result, have found that some esters of amino- or guanidino-1,2,3,4-tetrahydro-1-naphthoic acid show an inhibitory activity on proteolytic enzymes.

According to this invention, there are provided an amino- or guanidino-1,2,3,4-tetrahydro-1-naphthoic ester represented by the formula,

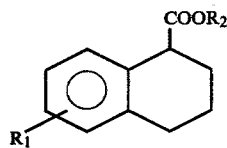

wherein $R_1$ is $-NH_2$ or

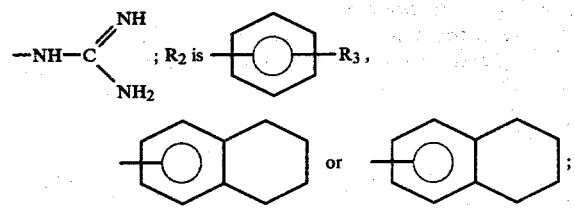

$R_3$ is $-H$, $-R_4$, $-O-R_4$, $-NHCOCH_3$, a halogen, $-CN$,

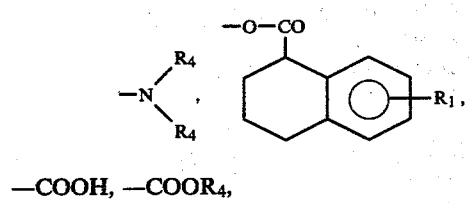

$-COOH$, $-COOR_4$,

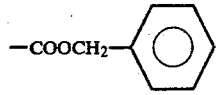

or $-(CH_2)_n-COOCH_2-CO-R_5$; $R_4$ is a lower alkyl; $R_5$ is $-O-R_4$, $-NH_2$ or

and n is 0, 1 or 2; and a pharmaceutically acceptable acid addition salt thereof.

The group $R_2$ in the formula (I) is phenyl; a lower alkylphenyl such as p-, m- or o-methylphenyl, p-, m- or o-ethylphenyl, p-, m- or o-n-propylphenyl, p-, m- or o-n-butylphenyl; a lower alkoxyphenyl such as p-, m- or o-methoxyphenyl, p-, m- or o-ethoxyphenyl, p-, m- or o-n-propoxyphenyl, p-, m- or o-n-butoxyphenyl; a lower alkoxycarbonylphenyl such as p-, m- or o-methoxycarbonylphenyl, p-, m- or o-ethoxycarbonylphenyl, p-, m- or o-n-propoxycarbonylpheyl, p-, m- or o-n-butoxycarbonylphenyl; p-, m- or o-benzyloxycarbonylphenyl; a halophenyl such as p-, m- or o-fluorophenyl, p-, m- or o-chlorophenyl, p-, m- or o-bromophenyl, p-, m- or o-iodophenyl; p-, m- or o-cyanophenyl; a di-lower alkylaminophenyl such as p-, m- or o-dimethylaminophenyl, p-, m- or o-diethylaminophenyl, p-, m- or o-di-n-propylaminophenyl, p-, m- or o-di-n-butylaminophenyl; p-, m- or o-acetoxyaminophenyl; p-, m- or o-carboxyphenyl; a lower alkoxycarbonylmethoxycarbonylphenyl such as p-, m- or o-methoxycarbonylmethoxycarbonylphenyl, p-, m- or o-ethoxycarbonylmethoxycarbonylphenyl, p-, m- or o-n-propoxycarbonylmethoxycarbonylphenyl, p-, m- or o-n-butoxycarbonylmethoxycarbonylphenyl; p-, m- or o-aminocarbonylmethoxycarbonylphenyl; a di-lower alkylaminocarbonylmethoxycarbonylphenyl, such as p-, m- or o-dimethylaminocarbonylmethoxycarbonylphenyl, p-, m- or o-diethylaminocarbonylmethoxycarbonylphenyl, p-, m- or o-di-n-propylaminocarbonylmethoxycarbonylphenyl, p-, m- or o-di-n-butylaminocarbonylmethoxycarbonylphenyl; a lower alkoxycarbonylmethoxycarbonylmethylphenyl such as p-, m- or o-ethoxycarbonylmethoxycarbonylmethylphenyl or the like; a lower alkoxycarbonylmethoxycarbonylethylphenyl such as p-, m- or o-ethoxycarbonylmethoxycarbonylethylphenyl or the like; a di-lower alkylaminocarbonylmethoxycarbonylmethylphenyl such as p-, m- or o-dimethylaminocarbonylmethoxycarbonylmethylphenyl, or the like; a lower alkylaminocarbonylmethoxycarbonylethylphenyl such as p-, m- or o-dimethylaminocarbonylmethoxycarbonylethylphenyl or the like; amino- or guanidino-1,2,3,4-tetrahydronaphthyl-1-carbonyloxyphenyl; 1,2,3,4-tetrahydronaphthyl; or naphthyl.

In the above-said group $R_2$, the lower alkyl group or lower alkoxy group has preferably 1 to 4 carbon atoms.

The pharmaceutically acceptable acid addition salts of the compounds represented by the formula (I) include carbonate, hydrochloride, hydrobromide, sulfate, phosphate, nitrate, acetate, lactate, oxalate, maleate, fumarate, tartrate, citrate, ascorbate, benzenesulfonate, toluenesulfonate, methanesulfonate and the like.

The compound of the formula (I) of this invention is prepared by subjecting to condensation a nitro-1,2,3,4-tetrahydro-1-naphthoic acid represented by the formula (II),

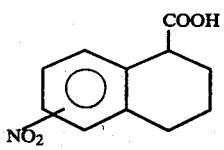

and a phenol derivative represented by the formula (III),

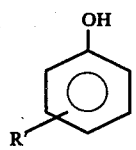

[R' is a hydrogen atom, a lower alkyl group, for example, methyl, ethyl, n-propyl, n-butyl or the like; a lower alkyl group, for example, methoxy, ethoxy, n-propoxy, n-butoxy or the like; a lower alkoxycarbonyl group, for example, methoxycarbonyl, ethoxycarbonyl, n-propoxycarbonyl, n-butoxycarbonyl or the like; a halogen atom, for example, fluorine, chlorine, bromine or iodine atom; methylcarbonylamino group; cyano group; a di-lower alkylamino group, for example, dimethylamino, diethylamino, di-n-propylamino, di-n-butylamino or the like; benzyloxycarbonyl group; a lower alkoxycarbonylmethoxycarbonyl group, for example, methoxycarbonylmethoxycarbonyl, ethoxycarbonylmethoxycarbonyl, n-propoxycarbonylmethoxycarbonyl, n-butoxycarbonylmethoxycarbonyl or the like; aminocarbonylmethoxycarbonyl group; a di-lower alkylaminocarbonylmethoxycarbonyl group, for example, dimethylaminocarbonylmethoxycarbonyl, diethylaminocarbonylmethoxycarbonyl, di-n-propylaminocarbonyl methoxycarbonyl or the like; a di-lower alkylaminocarbonylmethoxycarbonylmethyl group, for example, dimethylaminocarbonylmethoxycarbonylmethyl, diethylaminocarbonylmethoxycarbonylmethyl or the like; a lower alkoxycarbonylmethoxycarbonylmethyl group, for example, methoxycarbonylmethoxycarbonylmethyl, ethoxycarbonylmethoxycarbonylmethyl or the like; a di-lower alkylaminocarbonylmethoxycarbonylethyl group, for example, dimethylaminocarbonylmethoxycarbonylethyl, diethylaminocarbonylmethoxycarbonylethyl or the like; or hydroxyl group], a 1,2,3,4-tetrahydronaphthol represented by the formula (IV),

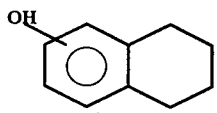

or a naphthol represented by the formula (V),

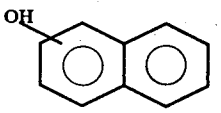

to yield a nitro-1,2,3,4-tetrahydro-1-naphthoic ester represented by the formula (VI)

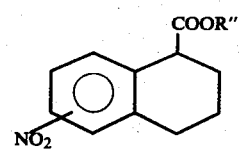

in which R'' is

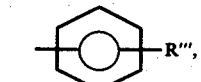

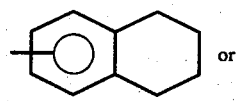

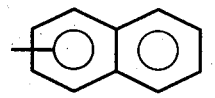

R''' is —H, —$R_4$, —O—$R_4$, —NHCOCH$_3$, a halogen,

—CN, —N$\begin{smallmatrix}R_4\\R_4\end{smallmatrix}$,

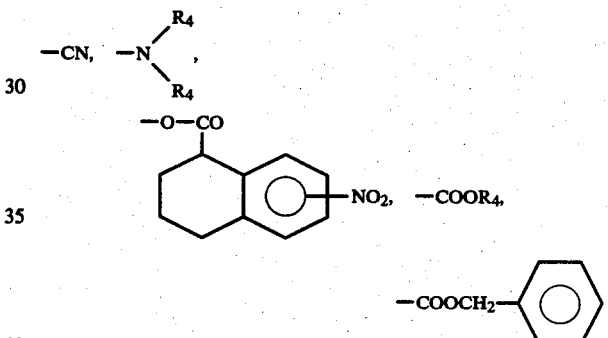

or —(CH$_2$)$_n$—COOCH$_2$—CO—$R_5$; and $R_4$, $R_5$ and n have the same meanings as defined above, then reducing the resulting ester to obtain an amino-1,2,3,4-tetrahydro-1-naphthoic ester represented by the formula (VII),

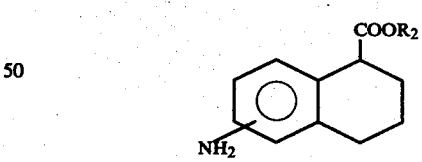

in which $R_2$ has the same meaning as defined above, and, if necessary, reacting this ester with cyanamide to form a guanidino-1,2,3,4-tetrahydro-1-naphthoic ester represented by formula (VIII),

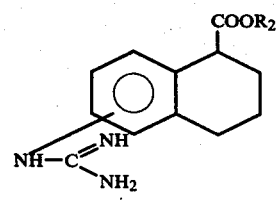

wherein R₂ has the same meaning as defined above. These reactions are shown by the following scheme:

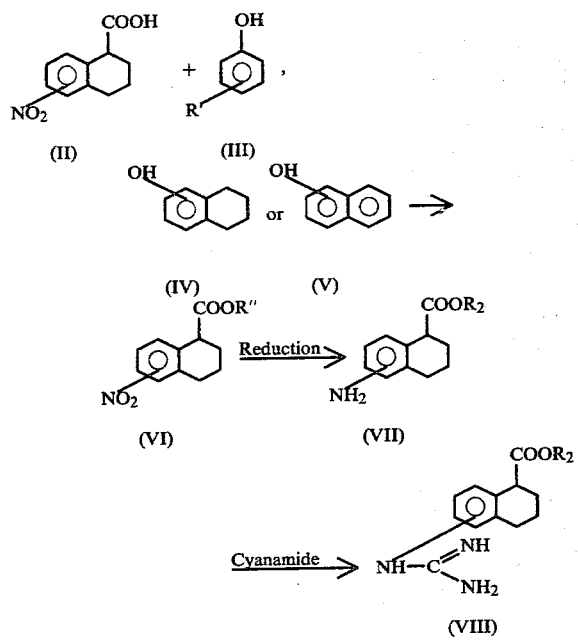

The starting material of the formula (II) used in the method of this invention is a known compound which is synthesized by the nitration of 1,2,3,4-tetrahydro-1-naphthoic acid. The other starting material represented by the formula (III) is also a known compound and includes phenol, p-, m- or o-methylphenol, p-, m- or o-ethylphenol, p-, m- or o-n-propylphenol, p-, m- or o-n-butylphenol, p-, m- or o-methoxyphenol, p-, m- or o-ethoxyphenol, p-, m- or o-n-propoxyphenol, p-, m- or o-n-butoxyphenol, p-, m- or o-methoxycarbonylphenol, p-, m- or o-ethoxycarbonylphenol, p-, m- or o-n-propoxycarbonylphenol, p-, m- or o-n-butoxycarbonylphenol, p-, m- or o-fluorophenol, p-, m- or o-chlorophenol, p-, m- or o-bromophenol, p-, m- or o-iodophenol, p-, m- or o-cyanophenol, p-, m- or o-dimethylaminophenol, p-, m- or o-diethylaminophenol, p-, m- or o-di-n-propylaminophenol, p-, m- or o-di-n-butylaminophenol, p-, m- or o-methylcarbonylaminophenol, p-, m- or o-benzyloxycarbonylphenol, p-, m- or o-methoxycarbonylmethoxycarbonylphenol, p-, m- or o-ethoxycarbonylmethoxycarbonylphenol, p-, m- or o-aminocarbonylmethoxycarbonylphenol, p-, m- or o-dimethylaminocarbonylmethoxycarbonylphenol, p-, m- or o-diethylaminocarbonylmethoxycarbonylphenol, p-, m- or o-dimethylaminocarbonylmethoxycarbonylmethylphenol, p-, m- or o-diethylaminocarbonylmethoxycarbonylmethylphenol, p-, m- or o-methoxycarbonylmethoxycarbonylethylphenol, p-, m- or o-ethoxycarbonylmethoxycarbonylethylphenol, p-, m- or o-dimethylaminocarbonylmethoxycarbonylethylphenol, p-, m- or o-diethylaminocarbonylmethoxycarbonylethylphenol, p-, m- or o-hydroxyphenol, etc.

In the process of this invention, at first, the starting material of the formula (II), and a phenol derivative of the formula (III), 1,2,3,4-tetrahydronaphthol of the formula (IV) or naphthol of the formula (V) are subjected to condensation by a known procedure to yield the compound of the formula (VI). The condensation can be effected by any of the well-known methods such as DCC (dicyclohexylcarbodiimide) method, DPPA (diphenyl phosphoryl azide) method, mixed acid anhydride method, and acyl chloride method. However, the acyl chloride method is the most favorable in view of the easiness of procedure, economy, and product purity. Since a hydrogen halide is liberated during the reaction when an acyl chloride is employed, it is advantageous to carry out the reaction in a solvent in the presence of a dehydrohalogenating agent such as an organic base, for example, triethylamine, tributylamine or pyridine or an inorganic base, for example, potassium carbonate or sodium carbonate. The solvents which may be used include benzene, ethyl acetate, diethyl ether, tetrahydrofuran, pyridine and the like. Of these, ethyl acetate is preferred in view of product purity.

The reaction proceeds with relative ease over a wide temperature range including room temperature as well as under mild cooling. It is generally completed in a period of 30 minutes to 1 hour at a temperature from 0° to 30° C. After the reaction, the compound of the formula (VI) is isolated in a conventional way.

The preparation of the amino-1,2,3,4-tetrahydro-1-naphthoic ester of the formula (VII) of this invention from the compound of the formula (VI) is easily performed by dissolving or suspending the isolated compound of the formula (VI) in an organic solvent and introducing hydrogen thereinto in the presence of a catalyst such as palladium-carbon, Raney nickel or platinum oxide or, alternatively, by adding the compound of the formula (VI) together with a powdered metal such as zinc or iron to an acid such as acetic acid or hydrochloric acid. The solvents suitable for the catalytic reduction include ethanol, methanol, dimethylformamide, tetrahydrofuran, diethyl ether, acetic acid and ethyl acetate. Of these solvents, ethanol, methanol and ethyl acetate are preferred. The reaction proceeds with relative ease over a wide temperature range including room temperature as well as under mild cooling. It is generally completed in a period of 1 to 2 hours at a temperature from 20° to 40° C. Isolation of the compound of the formula (VII) of this invention from the reaction mixture can be effected by a conventional method which comprises removing the catalyst from the reaction mixture by filtration and evaporating the filtrate under reduced pressure to remove the solvent.

The preparation of the guanidino-1,2,3,4-tetrahydro-1-naphthoic ester of the formula (VIII) of this invention from the corresponding amino-1,2,3,4-tetrahydro-1-naphthoic ester of the formula (VII) can be performed by reacting cyanamide with the compound of the formula (VII) either as such as dissolved or suspended in an organic solvent. The solvents suitable for use include ethanol, methanol, dimethylformamide, tetrahydrofuran and diethyl ether. Of these, ethanol and methanol and preferred. The reaction proceeds easily at a temperature in the range from room temperature to boiling point of the solvent. Isolation of the compound of the formula (VIII) from the reaction mixture can be performed by distilling the mixture under reduced pressure to remove the solvent. A purified compound of the formula (VIII) can be obtained, if desired, by recrystallization or column chromatography. If desired, an acid addition salt can be obtained from the compound (VII) or (VIII) in a conventional manner.

Nitro-1,2,3,4-tetrahydro-1-naphthoic esters of the formula (VI) are novel compounds having the physical properties as shown in Table 1.

Table 1

Structure: tetrahydronaphthalene with COOR" at position 1 and NO₂ substituent

| Compound No. | Position of —NO₂ | R" | Melting point (°C.) | IR (cm⁻¹) C=O |
|---|---|---|---|---|
| 1 | 5 | —C₆H₅ (phenyl) | 86–7 | 1740 |
| 2 | 5 | —C₆H₄—CH₃ (4-methylphenyl) | 87–9 | 1735 |
| 3 | 5 | —C₆H₄—Cl (4-chlorophenyl) | 127–9 | 1740 |
| 4 | 5 | —C₆H₄—N(CH₃)₂ | Oil | 1750 |
| 5 | 5 | —C₆H₄—CN | 136–8 | 1760 |
| 6 | 5 | —C₆H₄—OCH₃ (para) | 122–3 | 1740 |
| 7 | 5 | —C₆H₄—OCH₃ (meta) | Oil | 1750 |
| 8 | 5 | —C₆H₄—OCH₃ (ortho, H₃CO-) | 88–9 | 1750 |
| 9 | 5 | —C₆H₄—O(CH₂)₃CH₃ | 85–6 | 1740 |
| 10 | 5 | —C₆H₄—COOCH₃ (para) | 101–3 | 1740 |
| 11 | 5 | —C₆H₄—COOCH₃ (meta) | 79–80 | 1740 |
| 12 | 5 | —C₆H₄—COOCH₃ (ortho) | 98–9 | 1765 |
| 13 | 5 | —C₆H₄—COOCH₂CH₃ (para) | Oil | 1760 |
| 14 | 5 | —C₆H₄—COOCH₂CH₃ (ortho) | Oil | 1760 |
| 15 | 5 | —C₆H₄—COO(CH₂)₂CH₃ | Oil | 1750 |
| 16 | 5 | —C₆H₄—COOCH₂—C₆H₅ | 103–4 | 1740 |
| 17 | 5 | —C₆H₄—COOCH₂COOCH₂CH₃ | 85–6 | 1750 |
| 18 | 5 | —C₆H₄—COOCH₂CONH₂ | Oil | 1745 |
| 19 | 5 | —C₆H₄—COOCH₂CON(CH₃)₂ | 112–3 | 1750 |

Table 1-continued

[Structure: 1,2,3,4-tetrahydronaphthalene with COOR" at position 1 and NO₂ substituent]

| Compound No. | Position of —NO₂ | R" | Melting point (°C.) | IR (cm⁻¹) C=O |
|---|---|---|---|---|
| 20 | 5 | —C₆H₄—CH₂COOCH₂CON(CH₃)₂ | 105–7 | 1745 |
| 21 | 5 | —C₆H₄—CH₂CH₂COOCH₂COOCH₂CH₃ | 62–3 | 1760 |
| 22 | 5 | —C₆H₄—CH₂CH₂COOCH₂CON(CH₃)₂ | Oil | 1745 |
| 23 | 5 | —naphthyl (decalin) | Oil | 1750 |
| 24 | 5 | —naphthyl (tetralin) | 114–6 | 1740 |
| 25 | 5 | —C₆H₄—O—CO—(4-nitro-tetralinyl) | 153–5 | 1735 |
| 26 | 5 | —C₆H₄—NHCOCH₃ | 117–9 | 1740 |
| 27 | 7 | —C₆H₅ | 83–4 | 1740 |
| 28 | 7 | —C₆H₄—CH₃ | 81–2 | 1740 |
| 29 | 7 | —C₆H₄—Cl | 108–9 | 1740 |
| 30 | 7 | —C₆H₄—N(CH₃)₂ | Oil | 1750 |
| 31 | 7 | —C₆H₄—CN | 137–8 | 1745 |
| 32 | 7 | —C₆H₄—OCH₃ | 109–10 | 1735 |
| 33 | 7 | —C₆H₄—OCH₃ (meta) | Oil | 1750 |
| 34 | 7 | —C₆H₄—OCH₃ (ortho) | 81–2 | 1750 |
| 35 | 7 | —C₆H₄—O(CH₂)₃CH₃ | 108–10 | 1745 |
| 36 | 7 | —C₆H₄—COOCH₃ | 178–9 | 1745 |

Table 1-continued

[Structure: 1,2,3,4-tetrahydronaphthalene with COOR" at position 1 and NO₂ substituent]

| Compound No. | Position of —NO₂ | R" | Melting point (°C.) | IR (cm⁻¹) C=O |
|---|---|---|---|---|
| 37 | 7 | —C₆H₄—COOCH₃ (meta) | 100–3 | 1750 |
| 38 | 7 | —C₆H₄—COOCH₃ (ortho) | 105–6 | 1750 |
| 39 | 7 | —C₆H₄—COOCH₂CH₃ | 149–50 | 1750 |
| 40 | 7 | —C₆H₄—COOCH₂CH₃ (ortho) | Oil | 1760 |
| 41 | 7 | —C₆H₄—COO(CH₂)₂CH₃ | 115–7 | 1755 |
| 42 | 7 | —C₆H₄—COOCH₂—C₆H₅ | 115–6 | 1750 |
| 43 | 7 | —C₆H₄—COOCH₂COOCH₂CH₃ | 57–9 | 1750 |
| 44 | 7 | —C₆H₄—COOCH₂CONH₂ | 178–9 | 1745 |
| 45 | 7 | —C₆H₄—COOCH₂CON(CH₃)₂ | 150–2 | 1755 |
| 46 | 7 | —C₆H₄—CH₂COOCH₂CON(CH₃)₂ | 88–90 | 1755 |
| 47 | 7 | —C₆H₄—CH₂CH₂COOCH₂COOCH₂CH₃ | 99–100 | 1760 |
| 48 | 7 | —C₆H₄—CH₂CH₂COOCH₂CON(CH₃)₂ | Oil | 1745 |
| 49 | 7 | naphthyl | 122–3 | 1735 |
| 50 | 7 | naphthyl | 105–6 | 1745 |
| 51 | 7 | —C₆H₄—O—CO—(6-nitro-1,2,3,4-tetrahydronaphth-1-yl) | 156–7 | 1745 |
| 52 | 7 | —C₆H₄—NHCOCH₃ | 131 | 1745 |

The amino-1,2,3,4-tetrahydro-1-naphthoic esters of this invention of the formula (VII) and acid addition salts thereof have the physical properties as shown in Table 2.

Table 2

Structure: tetrahydronaphthalene with COOR₂ at position 1 and NH₂·X substituent

| Compound No. | Position of —NH₂ | R₂ | X | Melting point (°C.) | IR (cm⁻¹) C=O |
|---|---|---|---|---|---|
| 53 | 5 | —C₆H₅ | HCl | 216–8 | 1740 |
| 54 | 5 | —C₆H₄—CH₃ (para) | HCl | 220–2 | 1740 |
| 55 | 5 | —C₆H₄—Cl (para) | HCl | 232–4 | 1745 |
| 56 | 5 | —C₆H₄—N(CH₃)₂ (para) | 2HCl | Oil | 1750 |
| 57 | 5 | —C₆H₄—CN (para) | HCl | 208–10 | 1760 |
| 58 | 5 | —C₆H₄—OCH₃ (para) | HCl | 211–3 | 1735 |
| 59 | 5 | —C₆H₄—OCH₃ (meta) | HCl | 140–3 | 1750 |
| 60 | 5 | —C₆H₄—OCH₃ (ortho) | HCl | 210–2 | 1755 |
| 61 | 5 | —C₆H₄—O(CH₂)₃CH₃ | HCl | 215–7 | 1740 |
| 62 | 5 | —C₆H₄—COOH | HCl | 250 | 1750 |
| 63 | 5 | —C₆H₄—COOCH₃ (para) | HCl | 232–6 | 1740 |
| 64 | 5 | —C₆H₄—COOCH₃ (meta) | HCl | 170–3 | 1755 |
| 65 | 5 | —C₆H₄—COOCH₃ (ortho) | HCl | 217–8 | 1755 |
| 66 | 5 | —C₆H₄—COOCH₂CH₃ (para) | HCl | 218–9 | 1740 |
| 67 | 5 | —C₆H₄—COOCH₂CH₃ (ortho) | HCl | 140–3 | 1750 |
| 68 | 5 | —C₆H₄—COO(CH₂)₂CH₃ | HCl | 193–6 | 1740 |
| 69 | 5 | —C₆H₄—COOCH₂—C₆H₅ | HCl | 167–70 | 1750 |
| 70 | 5 | —C₆H₄—COOCH₂COOCH₂CH₃ | HCl | 183–4 | 1750 |
| 71 | 5 | —C₆H₄—COOCH₂CONH₂ | HCl | 209–11 | 1750 |

Table 2-continued

Structure: 1,2,3,4-tetrahydronaphthalene with COOR$_2$ at position 1 and NH$_2 \cdot$ X substituent

| Compound No. | Position of —NH$_2$ | R$_2$ | X | Melting point (°C.) | IR (cm$^{-1}$) C=O |
|---|---|---|---|---|---|
| 72 | 5 | —C$_6$H$_4$—COOCH$_2$CON(CH$_3$)$_2$ | HCl | 181–3 | 1750 |
| 73 | 5 | —C$_6$H$_4$—CH$_2$COOCH$_2$CON(CH$_3$)$_2$ | HCl | Oil | 1745 |
| 74 | 5 | —C$_6$H$_4$—CH$_2$CH$_2$COOCH$_2$COOCH$_2$CH$_3$ | HCl | 190–1 | 1760 |
| 75 | 5 | —C$_6$H$_4$—CH$_2$CH$_2$COOCH$_2$CON(CH$_3$)$_2$ | HCl | Oil | 1740 |
| 76 | 5 | naphthyl | HCl | 238–9 | 1750 |
| 77 | 5 | tetrahydronaphthyl | HCl | 233–5 | 1740 |
| 78 | 5 | —C$_6$H$_4$—O—CO—(5-amino-1,2,3,4-tetrahydronaphthalen-1-yl) | 2HCl | 243–4 | 1745 |
| 79 | 5 | —C$_6$H$_4$—NHCOCH$_3$ | Free | 174–5 | 1745 |
| 80 | 5 | —C$_6$H$_4$—NHCOCH$_3$ | HCl | 229–30 | 1745 |
| 81 | 7 | —C$_6$H$_5$ | Free | 89–90 | 1745 |
| 82 | 7 | —C$_6$H$_4$—CH$_3$ | HCl | 191–3 | 1745 |
| 83 | 7 | —C$_6$H$_4$—Cl | HCl | 175–7 | 1750 |
| 84 | 7 | —C$_6$H$_4$—N(CH$_3$)$_2$ | HCl | 147–9 | 1750 |
| 85 | 7 | —C$_6$H$_4$—CN | HCl | Oil | 1745 |
| 86 | 7 | —C$_6$H$_4$—OCH$_3$ | HCl | 55–6 | 1740 |
| 87 | 7 | —C$_6$H$_4$—OCH$_3$ (meta) | HCl | 150–2 | 1740 |
| 88 | 7 | —C$_6$H$_4$—OCH$_3$ (ortho) | HCl | Oil | 1750 |
| 89 | 7 | —C$_6$H$_4$—O(CH$_2$)$_3$CH$_3$ | HCl | Oil | 1750 |

Table 2-continued

Structure: 1-COOR₂, NH₂·X substituted tetrahydronaphthalene

| Compound No. | Position of —NH₂ | R₂ | X | Melting point (°C.) | IR (cm⁻¹) C=O |
|---|---|---|---|---|---|
| 90 | 7 | –C₆H₄–COOH | HCl | 257 | 1745 |
| 91 | 7 | –C₆H₄–COOCH₃ (para) | HCl | 204–8 | 1750 |
| 92 | 7 | –C₆H₄–COOCH₃ (meta) | HCl | 157–9 | 1745 |
| 93 | 7 | –C₆H₄–COOCH₃ (ortho) | HCl | Oil | 1750 |
| 94 | 7 | –C₆H₄–COOCH₂CH₃ (para) | HCl | 166–7 | 1750 |
| 95 | 7 | –C₆H₄–COOCH₂CH₃ (ortho) | HCl | 150–2 | 1740 |
| 96 | 7 | –C₆H₄–COO(CH₂)₂CH₃ | HCl | 133–7 | 1750 |
| 97 | 7 | –C₆H₄–COOCH₂–C₆H₅ | HCl | 163–4 | 1750 |
| 98 | 7 | –C₆H₄–COOCH₂COOCH₂CH₃ | HCl | 146–7 | 1750 |
| 99 | 7 | –C₆H₄–COOCH₂CONH₂ | HCl | Oil | 1750 |
| 100 | 7 | –C₆H₄–COOCH₂CON(CH₃)₂ | HCl | Oil | 1750 |
| 101 | 7 | –C₆H₄–CH₂COOCH₂CON(CH₃)₂ | HCl | Oil | 1755 |
| 102 | 7 | –C₆H₄–CH₂CH₂COOCH₂COOCH₂CH₃ | HCl | Oil | 1755 |
| 103 | 7 | –C₆H₄–CH₂CH₂COOCH₂CON(CH₃)₂ | HCl | Oil | 1740 |
| 104 | 7 | naphthyl | HCl | 82–3 | 1740 |
| 105 | 7 | naphthyl | HCl | Oil | 1740 |
| 106 | 7 | –C₆H₄–O–CO–(7-amino-tetrahydronaphthalen-1-yl) | 2HCl | 98–100 | 1745 |
| 107 | 7 | –C₆H₄–NHCOCH₃ | Free | 172–3 | 1730 |
| 108 | 7 | –C₆H₄–NHCOCH₃ | HCl | 140–4 | 1745 |

The guanidino-1,2,3,4-tetrahydro-1-naphthoic esters of the formula (VIII) of this invention and acid addition salts thereof have the physical properties as shown in Table 3.

Table 3

| Compound No. | Position of $-\underset{H}{N}-C\underset{NH_2}{\overset{NH}{\diagup}}$ | $R_2$ | X | Melting point (°C.) | IR (cm$^{-1}$) C=O |
|---|---|---|---|---|---|
| 109 | 5 | 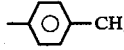 | HCl | Oil | 1750 |
| 110 | 5 | —CH$_3$ | HCl | Oil | 1740 |
| 111 | 5 | 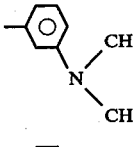—Cl | HCl | Oil | 1740 |
| 112 | 5 | 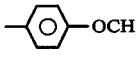—N(CH$_3$)$_2$ | 2HCl | Oil | 1740 |
| 113 | 5 | 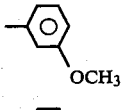—OCH$_3$ | HCl | Oil | 1740 |
| 114 | 5 | 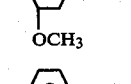 OCH$_3$ | HCl | Oil | 1745 |
| 115 | 5 | 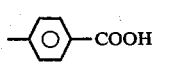 OCH$_3$ | HCl | Oil | 1750 |
| 116 | 5 | 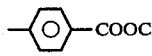—O(CH$_2$)$_3$CH$_3$ | HCl | Oil | 1740 |
| 117 | 5 | —COOH | HCl | Oil | 1750 |
| 118 | 5 | 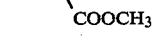—COOCH$_3$ | HCl | Oil | 1745 |
| 119 | 5 |  COOCH$_3$ | HCl | Oil | 1750 |
| 120 | 5 | 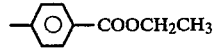 COOCH$_3$ | HCl | Oil | 1755 |
| 121 | 5 | —COOCH$_2$CH$_3$ | HCl | Oil | 1750 |
| 122 | 5 | 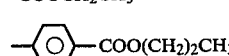 COOCH$_2$CH$_3$ | HCl | Oil | 1750 |
| 123 | 5 | —⟨O⟩—COO(CH$_2$)$_2$CH$_3$ | HCl | Oil | 1750 |

Table 3-continued

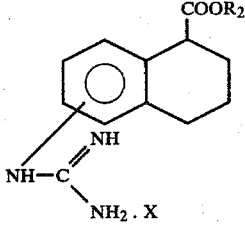

| Compound No. | Position of $-\underset{H}{N}-\underset{\|NH_2}{\overset{\|NH}{C}}$ | R$_2$ | X | Melting point (°C.) | IR (cm$^{-1}$) C=O |
|---|---|---|---|---|---|
| 124 | 5 | -C$_6$H$_4$-COOCH$_2$-C$_6$H$_5$ | HCl | Oil | 1750 |
| 125 | 5 | -C$_6$H$_4$-COOCH$_2$COOCH$_2$CH$_3$ | HCl | Oil | 1750 |
| 126 | 5 | -C$_6$H$_4$-COOCH$_2$CONH$_2$ | HCl | Oil | 1745 |
| 127 | 5 | -C$_6$H$_4$-COOCH$_2$CON(CH$_3$)$_2$ | HCl | Oil | 1745 |
| 128 | 5 | -C$_6$H$_4$-CH$_2$COOCH$_2$CON(CH$_3$)$_2$ | HCl | Oil | 1745 |
| 129 | 5 | -C$_6$H$_4$-CH$_2$CH$_2$COOCH$_2$COOCH$_2$CH$_3$ | HCl | Oil | 1755 |
| 130 | 5 | -C$_6$H$_4$-CH$_2$CH$_2$COOCH$_2$CON(CH$_3$)$_2$ | HCl | Oil | 1740 |
| 131 | 5 | -naphthyl | HCl | Oil | 1745 |
| 132 | 5 | -C$_6$H$_4$-O-CO-(tetrahydronaphthyl-guanidine) | 2HCl | Oil | 1735 |
| 133 | 5 | -C$_6$H$_4$-NHCOCH$_3$ | HCl | Oil | 1745 |
| 134 | 7 | -C$_6$H$_5$ | HCl | Oil | 1740 |
| 135 | 7 | -C$_6$H$_5$ | H$_2$CO$_3$ | 106 | 1750 |
| 136 | 7 | -C$_6$H$_4$-CH$_3$ | HCl | Oil | 1735 |
| 137 | 7 | -C$_6$H$_4$-Cl | HCl | Oil | 1740 |
| 138 | 7 | -C$_6$H$_4$-OCH$_3$ | HCl | Oil | 1735 |
| 139 | 7 | -C$_6$H$_4$-OCH$_3$ (meta) | HCl | Oil | 1745 |
| 140 | 7 | -C$_6$H$_4$-OCH$_3$ | HCl | Oil | 1750 |
| 141 | 7 | -C$_6$H$_4$-OCH$_3$ | CH$_3$SO$_3$H | 146–50 | 1750 |

Table 3-continued

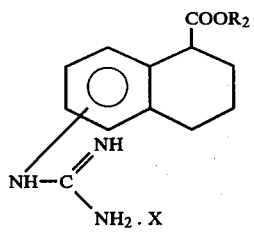

| Compound No. | Position of −N(H)−C(=NH)NH₂ | R₂ | X | Melting point (°C.) | IR (cm⁻¹) C=O |
|---|---|---|---|---|---|
| 142 | 7 | —⟨C₆H₄⟩—O(CH₂)₃CH₃ | HCl | Oil | 1745 |
| 143 | 7 | —⟨C₆H₄⟩—COOH | HCl | Oil | 1745 |
| 144 | 7 | —⟨C₆H₄⟩—COOCH₃ | HCl | Oil | 1750 |
| 145 | 7 | —⟨C₆H₄⟩(COOCH₃) (meta) | HCl | Oil | 1750 |
| 146 | 7 | —⟨C₆H₄⟩(COOCH₃) (ortho) | HCl | Oil | 1750 |
| 147 | 7 |  | CH₃SO₃H | 95–100 | 1750 |
| 148 | 7 | —⟨C₆H₄⟩—COOCH₂CH₃ | HCl | Oil | 1755 |
| 149 | 7 |  | CH₃SO₃H | 162-5 | 1760 |
| 150 | 7 | —⟨C₆H₄⟩(COOCH₂CH₃) (meta) | HCl | Oil | 1750 |
| 151 | 7 | —⟨C₆H₄⟩—COO(CH₂)₂CH₃ | HCl | Oil | 1750 |
| 152 | 7 | —⟨C₆H₄⟩—COOCH₂—⟨C₆H₅⟩ | HCl | Oil | 1750 |
| 153 | 7 | —⟨C₆H₄⟩—COOCH₂COOCH₂CH₃ | HCl | Oil | 1750 |
| 154 | 7 | —⟨C₆H₄⟩—COOCH₂CONH₂ | HCl | Oil | 1745 |
| 155 | 7 | —⟨C₆H₄⟩—COOCH₂CON(CH₃)₂ | HCl | Oil | 1745 |
| 156 | 7 | —⟨C₆H₄⟩—CH₂COOCH₂CON(CH₃)₂ | HCl | Oil | 1755 |
| 157 | 7 | —⟨C₆H₄⟩—CH₂CH₂COOCH₂COOCH₂CH₃ | HCl | Oil | 1745 |
| 158 | 7 | —⟨C₆H₄⟩—CH₂CH₂COOCH₂CON(CH₃)₂ | HCl | Oil | 1740 |
| 159 | 7 | —⟨naphthyl⟩ | HCl | Oil | 1745 |

Table 3-continued

| Compound No. | Position of -N(H)-C(=NH)NH$_2$ | R$_2$ | X | Melting point (°C.) | IR (cm$^{-1}$) C=O |
|---|---|---|---|---|---|
| 160 | 7 | —⟨O⟩—O—CO— [naphthyl-NH-C(=NH)NH$_2$] | 2HCl | Oil | 1735 |
| 161 | 7 | —⟨O⟩—NHCOCH$_3$ | HCl | Oil | 1735 |
| 162 | 5 | —⟨O⟩—CN | HCl | Oil | 1750 |
| 163 | 7 | —⟨O⟩—CN | HCl | Oil | 1750 |
| 164 | 5 | —[tetrahydronaphthyl] | HCl | Oil | 1740 |
| 165 | 5 | —[tetrahydronaphthyl] | H$_2$SO$_3$ | 100–3 | 1740 |
| 166 | 5 | —[tetrahydronaphthyl] | H$_3$C—⟨O⟩—SO$_3$H | 177–80 | 1750 |
| 167 | 7 | —[tetrahydronaphthyl] | HCl | Oil | 1740 |
| 168 | 7 | —[tetrahydronaphthyl] | H$_2$CO$_3$ | 98–100 | 1740 |

The invention is illustrated below in detail with reference to Examples which are merely illustrative and not limitative.

EXAMPLE 1

Synthesis of p-ethoxycarbonylphenyl 5-amino-1,2,3,4-tetrahydro-1-naphthoate hydrochloride (Compound No. 66)

In 50 ml of ethyl acetate was dissolved 5 g of 5-nitro-1,2,3,4-tetrahydro-1-naphthoic acid. After addition of 4.6 g of phosphorus pentachloride to the resulting solution at room temperature, the mixture was stirred for 30 minutes. The precipitates were removed by filtration and the filtrate was freed from ethyl acetate by distillation under reduced pressure. The residue was dissolved in 100 ml of fresh ethyl acetate. To the solution were added, with cooling, 4.1 g of p-ethoxycarbonylphenol and 2.5 g of triethylamine. The mixture was stirred for 24 hours. The reaction mixture was washed with a cold 5% sodium hydroxide solution and freed from the solvent by distillation to obtain 7.2 g (80% yield) of oily p-ethoxycarbonylphenyl 5-nitro-1,2,3,4-tetrahydro-1-naphthoate.

IR (liquid) cm$^{-1}$: 1750, 1712 (two ester groups), 1350 (nitro group).

NMR (d$_6$-acetone) ppm: 8.06 (2H, d, J=8.8), 7.29 (2H, d, J=8.8), 7.82–7.18 (3H), 4.34 (2H, q, J=7.1), 1.36 (3H, t, J=7.1).

A 5.2-g portion of the p-ethoxycarbonylphenyl 5-nitro-1,2,3,4-tetrahydro-1-naphthoate obtained above was catalytically reduced with 5% palladium-carbon in ethyl acetate. After removal of the catalyst by filtration, the ethyl acetate was removed by distillation to obtain p-ethoxycarbonylphenyl 5-amino-1,2,3,4-tetrahydro-1-naphthoate which was dissolved in diethyl ether and dry gaseous hydrogen chloride was introduced thereinto to obtain 4.5 g of p-ethoxycarbonylphenyl 5-amino- 1,2,3,4-tetrahydro-1-naphthoate hydrochloride, m.p. 218°–219° C.

IR (KBr) cm$^{-1}$: 1740, 1710 (two carbonyl groups), 2900 (—NH$_2$).

This compound inhibited the tosylarginine methyl ester hydrolyzing activity of trypsin in vitro, and the concentration of said compound at which the hydrolysis was inhibited by 50% (ID$_{50}$) was $8.8 \times 10^{-5}$ M. However, it had no inhibitory activity on plasmin, Cl-esterase, kallikrein and thrombin.

EXAMPLE 2

Synthesis of p-chlorophenyl 7-amino-1,2,3,4-tetrahydro-1-naphthoate hydrochloride (Compound No. 83)

In 10 ml of ethyl acetate was dissolved 1 g of 7-nitro-1,2,3,4-tetrahydro-1-naphthoic acid. After addition of 0.94 g of phosphorus pentachloride at room temperature, the mixture was stirred for 30 minutes. The precipitates were removed by filtration and the filtrate was freed from ethyl acetate by distillation under reduced pressure. The residue was dissolved in 20 ml of fresh ethyl acetate. To the solution were added, with cooling, 0.6 g of p-chlorophenol and 0.5 g of triethylamine and the resulting solution was allowed to stand overnight. The reaction mixture was washed with a cold 5% sodium hydroxide solution and the organic layer was concentrated under reduced pressure. The residue was recrystallized from a benzene-hexane mixture to obtain 700 mg of p-chlorophenyl 7-nitro-1,2,3,4-tetrahydro-1-naphthoate, m.p. 108°–109° C.

IR (KBr) cm$^{-1}$: 1742 (ester group), 1350 (nitro group).

NMR (d$_6$-acetone) ppm: 8.26 (1H, d, J=2.0), 7.45 (2H, d, J=9.03), 7.20 (2H, d, J=9.03).

A 330-mg portion of the p-chlorophenyl 7-nitro-1,2,3,4-tetrahydro-1-naphthoate obtained above was dissolved in 10 ml of acetic acid and the resulting solution was slowly added dropwise at room temperature to 10 ml of acetic acid containing 2 g of zinc dust. After 30 minutes the precipitates were removed by filtration and the filtrate was concentrated under reduce pressure. The residue was dissolved in ethyl acetate and washed with a 5% aqueous sodium hydrogen carbonate solution. The ethyl acetate layer was concentrated under reduced pressure. The residue was dissolved in diethyl ether and dry gaseous hydrogen chloride was introduced thereinto to obtain 290 mg of p-chlorophenyl 7-amino-1,2,3,4-tetrahydro-1-naphthoate hydrochloride having a melting point of 175°–177° C.

IR (KBr) cm$^{-1}$: 2950 (—NH$_2$), 1745 (ester group).

This compound inhibited the tosylarginine methyl ester hydrolyzing activity of trypsin in vitro. The ID$_{50}$ of this compound was $2.7 \times 10^{31}$ $^4$ M. However, it had no inhibitory action on plasmin, Cl-esterase, kallikrein and thrombin.

EXAMPLE 3

The procedures of Example 1 were repeated, except that phenol, phenol derivatives and naphthol corresponding to R$_2$ in Table 2 were used as starting phenol derivatives. The intended compounds obtained were as shown in Table 2.

EXAMPLE 4

Synthesis of p-methoxyphenyl 7-guanidino-1,2,3,4-tetrahydro-1-naphthoate hydrochloride (Compound No. 138)

In 20 ml of pyridine were dissolved 1 g of 7-nitro-1,2,3,4-tetrahydro-1-naphthoic acid and 560 mg of p-methoxyphenol. To the solution which had been cooled was added 700 mg of phosphorus oxychloride and the mixture was allowed to stand for 2 days. The reaction mixture was poured into ice water, made slightly alkaline with a 5% sodium hydrogen carbonate solution and extracted with ethyl acetate. The ethyl acetate layer was separated and concentrated under reduced pressure to remove the ethyl acetate. The residue was recrystallized from an ethyl acetate-hexane mixture to obtain 0.8 g of p-methoxyphenyl 7-nitro-1,2,3,4-tetrahydro-1-naphthoate, m.p. 109°–110° C.

IR (KBr) cm$^{-1}$: 1735 (ester), 1350 (nitro group).

A 0.8-g portion of the p-methoxyphenyl 7-nitro-1,2,3,4-tetrahydro-1-naphthoate obtained above was catalytically reduced with 5% palladium-carbon in acetic acid. After removal of the catalyst by filtration, the acetic acid was removed by distillation under reduced pressure to obtain p-methoxyphenyl 7-amino-1,2,3,4-tetrahydro-1-naphthoate, which was then dissolved in diethyl ether, and dry gaseous hydrogen chloride was introduced into the resulting solution to obtain 520 mg of p-methoxyphenyl 7-amino-1,2,3,4-tetrahydro-1-naphthoate hydrochloride, m.p. 155°–156° C.

IR (KBr) cm$^{-1}$: 2950 (—NH$_2$), 1740 (ester).

A 500-mg portion of the p-methoxyphenyl 7-amino-1,2,3,4-tetrahydro-1-naphthoate hydrochloride obtained above and 250 mg of crystalline cyanamide were placed in a flask, admixed with a small amount of ethanol and allowed to stand at 50° C. for 2 days. The reaction mixture was freed from ethanol by distillation under reduced pressure to remove the ethanol. The residue was purified by silica gel column chromatography to obtain 480 mg of p-methoxyphenyl 7-guanidino-1,2,3,4-tetrahydro-1-naphthoate hydrochloride in the oily form.

IR (liquid) cm$^{-1}$: 1735.

This compound inhibited the tosylarginine methyl ester hydrolyzing activity of thrombin in vitro. The ID$_{50}$ was $3.2 \times 10^{-5}$ M.

EXAMPLE 5

Synthesis of phenyl 7-guanidino-1,2,3,4-tetrahydro-1-naphthoate hydrochloride (Compound No. 134)

In 50 ml of ethyl acetate was dissolved 1.5 g of 7-nitro-1,2,3,4-tetrahydro-1-naphthoic acid. To the resulting solution was added at room temperature 1.3 g of phosphorus pentachloride, and the mixture was stirred for 30 minutes. The precipitates were removed by filtration and the filtrate was concentrated under reduced pressure. The residue was dissolved in 50 ml of fresh ethyl acetate. To the solution were added with cooling 1.0 g of phenol and 8.5 g of triethylamine. The resulting mixture was stirred for 24 hours. The reaction mixture was washed with a cold 5% sodium hydroxide solution and freed from the solvent by distillation to obtain 1.5 g of phenyl 7-nitro-1,2,3,4-tetrahydro-1-naphthoate having a melting point of 83°–84° C.

IR (KBr) cm$^{-1}$: 1740 (ester), 1350 (nitro group).

NMR (d$_6$-acetone) ppm: 8.26 (1H, d, J=2.0), 8.04 (1H, d, d, J=8.4, 2.0).

A 1.0-g portion of the phenyl 7-nitro-1,2,3,4-tetrahydro-1-naphthoate obtained above was catalytically reduced with 5% palladium-carbon in ethyl acetate. After removal of the catalyst by filtration, the ethyl acetate was removed by distillation under reduced pressure. The residue was recrystallized from methanol to obtain 550 mg of phenyl 7-amino-1,2,3,4-tetrahydro-1-naphthoate, m.p. 89°–90° C.

A 300-mg portion of the phenyl 7-amino-1,2,3,4-tetrahydro-1-naphthoate obtained above, 0.5 ml of 10% hydrochloric acid and 250 mg of crystalline cyanamide were placed in a flask, and a small amount of ethanol was added thereto, after which the resulting mixture was heated to about 50° C. and allowed to stand overnight. The reaction mixture was freed from the ethanol by distillation under reduced pressure and purified by silica gel column chromatography to obtain 250 mg of phenyl 7-guanidino-1,2,3,4-tetrahydro-1-naphthoate hydrochloride in the oily form.

IR (liquid) cm$^{-1}$: 1740.

This compound inhibited the tosylarginine methyl ester hydrolyzing action of thrombin. The ID$_{50}$ was $2.7 \times 10^{-5}$ M. It also had an inhibitory activity on Cl-esterase and kallikrein but no activity at all on plasmin.

EXAMPLE 6

Synthesis of ethoxycarbonylphenyl 5-guanidino-1,2,3,4-tetrahydro-1-naphthoate hydrochloride (Compound No. 121)

In a flask were placed 3.0 g of p-ethoxy carbonylphenyl 5-amino-1,2,3,4-tetrahydro-1-naphthoate hydrochloride synthesized from 5-nitro-1,2,3,4-tetrahydro-1-naphthoate acid and p-ethoxycarbonylphenol in the same manner as in Example 5, 1.5 g of crystalline cyanamide and a small amount of ethanol. The mixture was heated at 50° C. for 2 days and then freed from the ethanol by distillation under reduced pressure. The residue was purified by silica gel column chromatography to obtain 1.8 g of ethoxycarbonylphenyl 5-guanidino-1,2,3,4-tetrahydro-1-naphthoate hydrochloride in the oily form.

IR (liquid) cm$^{-1}$: 1750 (ester).

The compound inhibited the tosylarginine methyl ester hydrolyzing activity of trypsin. The ID$_{50}$ was $7.4 \times 10^{-5}$.

EXAMPLE 7

The procedure of Example 4 was repeated, except that phenol, phenol derivatives and naphthol corresponding to R$_2$ in Table 3 were used as starting phenol derivatives, to obtain the objective compounds as shown in Table 3.

APPLICATION EXAMPLE (A) Determination of Enzyme-inhibitory Activity

The enzyme-inhibitory activities in vitro of the compounds of this invention were measured by the following procedure according to the method of M. Muramatsu et al. [M. Muramatsu, T. Onishi, S. Makino, Y. Hayashi and S. Fujii: J. Biochem., 58, 214 (1965)]

(1) Inhibitory Effect on Ester-Hydrolyzing Activity of Trypsin

To 0.1 ml of trypsin (5 μg/ml) were added 0.5 ml of 0.1 M borate buffer solution (pH 8.6) containing 10 mM CaCl$_2$, and 0.1 ml of a varying concentration of an inhibitor solution, and preincubation was carried out at 37° C. for 5 minutes. Then, 10 μmoles of the substrate, TAMe (tosylarginine methyl ester), was added, and incubation was preformed at 37° C. for 30 minutes.

After the incubation, 1.5 ml of 2 M alkaline hydroxylamine was added and thoroughly mixed, and allowed to stand at room temperature for 15 minutes. Then, 1.0 ml of each of 18% trichloroacetic acid, 4 N HCl and 10% FeCl$_3$ was added and thoroughly mixed. If necessary, the mixture was centrifuged at 3,000 rpm for 10 minutes, and the absorbance of the supernatant was measured at 530 nm.

(2) Inhibitory Effect on Ester-Hydrolyzing Activity of Human Plasmin

It was measured by using 0.1 ml of plasmin (generated by activation of plasminogen with streptokinase) and TAMe as substrate following the method described in (1).

(3) Inhibitory Effect on Ester-Hydrolyzing Activity of Human Plasma Kallikrein

It was measured by using 0.5 ml of kallikrein (generated by activation of kallikreinogen with acetone), and TAMe as substrate following the method described in (1).

(4) Inhibitory Effect on Ester-Hydrolyzing Activity of Bovine Thrombin

It was measured by using 0.4 ml of bovine thrombin (1 μ/ml), 0.02 M sodium phosphate buffer solution (pH 7.4) and TAMe as substrate following the method described in (1).

(5) Inhibitory Effect on Ester-Hydrolying Activity of Human Cl Esterase [K. Okamura, M. Muramatsu, and S. Fujii: Biochem. Biophys. Acta, 295 252–257 (1973)].

It was measured by using 0.1 ml of Cl esterase, 0.1 ml of 0.02 M sodium phosphate buffer solution (pH 7.4) and 10 μmoles of ATEe (acetyltyrosine ethyl ester) as substrate following the method described in (1).

Enzyme-inhibitory activities (percent inhibition at 10$^{-3}$M or ID$_{50}$) of the compounds are shown in Table 4.

Table 4

| Compound No. | Trypsin | Plasmin | Cl-esterase | Kallikrein | Thrombin |
|---|---|---|---|---|---|
| 63 | [$1.8 \times 10^{-5}$] | 35.0 | 16.5 | — | [$1.0 \times 10^{-3}$] |
| 64 | [$6.1 \times 10^{-5}$] | NE | NE | 28.0 | 20.3 |
| 66 | [$8.8 \times 10^{-5}$] | 4.4 | NE | 19.9 | 16.5 |
| 68 | [$4.1 \times 10^{-5}$] | NE | NE | — | NE |
| 70 | [$5.2 \times 10^{-5}$] | 26.2 | NE | 14.1 | 22.0 |
| 71 | [$3.1 \times 10^{-5}$] | [$5.4 \times 10^{-5}$] | 30.6 | 23.4 | [$6.2 \times 10^{-5}$] |

Table 4-continued

| Compound No. | Trypsin | Plasmin | Cl-esterase | Kallikrein | Thrombin |
|---|---|---|---|---|---|
| 72 | $[2.5 \times 10^{-5}]$ | NE | NE | $[1.0 \times 10^{-3}]$ | $[1.2 \times 10^{-4}]$ |
| 78 | $[3.6 \times 10^{-5}]$ | NE | 15.2 | $[3.6 \times 10^{-4}]$ | 24.4 |
| 91 | $[1.7 \times 10^{-5}]$ | 40.7 | 27.4 | — | $[2.1 \times 10^{-4}]$ |
| 92 | $[9.8 \times 10^{-5}]$ | NE | 27.3 | NE | $[1.0 \times 10^{-3}]$ |
| 94 | $[4.6 \times 10^{-5}]$ | 16.6 | 3.2 | 25.0 | 42.9 |
| 96 | $[6.8 \times 10^{-5}]$ | NE | NE | — | 25.1 |
| 98 | $[6.0 \times 10^{-5}]$ | 24.6 | NE | NE | 40.5 |
| 99 | $[8.8 \times 10^{-5}]$ | $[3.0 \times 10^{-4}]$ | $[5.4 \times 10^{-4}]$ | 17.2 | $[6.6 \times 10^{-5}]$ |
| 100 | $[1.9 \times 10^{-4}]$ | $[5.3 \times 10^{-5}]$ | 42.0 | 36.0 | $[4.0 \times 10^{-5}]$ |
| 101 | $[1.1 \times 10^{-4}]$ | $[4.8 \times 10^{-5}]$ | 31.5 | 34.4 | $[3.0 \times 10^{-4}]$ |
| 103 | $[7.8 \times 10^{-5}]$ | 21.5 | 27.2 | 13.3 | $[1.0 \times 10^{-3}]$ |
| 106 | $[9.2 \times 10^{-5}]$ | NE | 31.0 | NE | 35.0 |
| 111 | 19.0 | NE | $[6.8 \times 10^{-4}]$ | NE | 18.6 |
| 116 | NE | $[1.0 \times 10^{-3}]$ | $[3.5 \times 10^{-4}]$ | 29.3 | $[1.0 \times 10^{-3}]$ |
| 118 | $[1.0 \times 10^{-3}]$ | $[1.0 \times 10^{-3}]$ | $[7.8 \times 10^{-4}]$ | — | $[8.0 \times 10^{-5}]$ |
| 123 | 45.7 | $[9.0 \times 10^{-4}]$ | $[3.5 \times 10^{-4}]$ | — | 46.7 |
| 124 | $[7.5 \times 10^{-5}]$ | $[6.0 \times 10^{-5}]$ | $[1.0 \times 10^{-3}]$ | $[1.9 \times 10^{-4}]$ | 45.0 |
| 126 | $[7.5 \times 10^{-5}]$ | $[5.8 \times 10^{-4}]$ | 30.6 | 46.9 | $[2.9 \times 10^{-4}]$ |
| 131 | $[8.3 \times 10^{-4}]$ | 13.8 | $[4.1 \times 10^{-4}]$ | $[1 \times 10^{-3}]$ | NE |
| 134 | 40.6 | NE | $[3.7 \times 10^{-4}]$ | $[2.9 \times 10^{-4}]$ | $[2.7 \times 10^{-5}]$ |
| 136 | 17.5 | NE | $[5.4 \times 10^{-4}]$ | NE | $[9.0 \times 10^{-4}]$ |
| 137 | $[7.8 \times 10^{-5}]$ | $[1.0 \times 10^{-3}]$ | $[2.5 \times 10^{-4}]$ | $[1.2 \times 10^{-4}]$ | $[4.5 \times 10^{-5}]$ |
| 138 | $[1.0 \times 10^{-3}]$ | 17.0 | 39.0 | $[2.8 \times 10^{-4}]$ | $[3.2 \times 10^{-5}]$ |
| 139 | 46.0 | $[1.0 \times 10^{-3}]$ | $[4.5 \times 10^{-4}]$ | 36.7 | $[2.6 \times 10^{-4}]$ |
| 142 | 36.9 | $[3.6 \times 10^{-4}]$ | $[4.6 \times 10^{-4}]$ | $[7.6 \times 10^{-5}]$ | $[2.4 \times 10^{-5}]$ |
| 144 | $[1.4 \times 10^{-5}]$ | $[4.5 \times 10^{-5}]$ | $[3.1 \times 10^{-4}]$ | — | $[1.9 \times 10^{-5}]$ |
| 148 | $[1.5 \times 10^{-4}]$ | $[1.4 \times 10^{-4}]$ | $[2.6 \times 10^{-4}]$ | $[1.7 \times 10^{-4}]$ | $[6.0 \times 10^{-6}]$ |
| 151 | $[1.0 \times 10^{-4}]$ | $[4.8 \times 10^{-4}]$ | $[3.3 \times 10^{-4}]$ | — | $[4.2 \times 10^{-5}]$ |
| 157 | 48.8 | $[2.1 \times 10^{-4}]$ | $[4.2 \times 10^{-4}]$ | 48.5 | $[1.2 \times 10^{-4}]$ |
| 158 | 29.1 | $[4.0 \times 10^{-4}]$ | $[7.0 \times 10^{-4}]$ | $[4.2 \times 10^{-4}]$ | $[1.0 \times 10^{-4}]$ |
| 159 | $[3.2 \times 10^{-4}]$ | 27.6 | $[1.8 \times 10^{-4}]$ | $[1.1 \times 10^{-4}]$ | 46.0 |
| 160 | 40.5 | $[1.0 \times 10^{-4}]$ | $[4.3 \times 10^{-4}]$ | $[2.3 \times 10^{-4}]$ | $[5.4 \times 10^{-5}]$ |
| 162 | 44.2 | 49.0 | 26.4 | $[1.0 \times 10^{-3}]$ | $[1.0 \times 10^{-3}]$ |
| 163 | $[1.3 \times 10^{-4}]$ | $[7.3 \times 10^{-5}]$ | $[4.0 \times 10^{-4}]$ | $[5.2 \times 10^{-5}]$ | $[1.7 \times 10^{-5}]$ |
| 164 | $[1.0 \times 10^{-3}]$ | 46.1 | $[4.0 \times 10^{-4}]$ | $[1.0 \times 10^{-3}]$ | NE |
| 167 | 44.8 | $[1.0 \times 10^{-3}]$ | $[4.2 \times 10^{-4}]$ | $[2.0 \times 10^{-4}]$ | NE |

Note: NE = not effective; [ ] = $ID_{50}(M)$ (B) Inhibitory Activity on Plasma Clotting Blood was drawn from carotid artery of an ether anesthetized rabbit with 1/10 volume of 3.8% sodium citrate. Platelet poor plasma (PPP) was prepared from citrated blood which was centrifuged at 3,000 r.p.m. for 15 minutes at 4° C. PPP, 0.9 ml, was taken into cell, 10μ of a compound solution was added and incubated at 37° C. for 10 minutes. Subsequently, 0.1 ml of thrombin solution was added and the change in absorbance of PPP resulting from processes of clotting was determined by means of aggregation meter (Evans Electroselenium Ltd. model 169). Compounds were dissolved in distilled water or 50% dimethyl sulfoxide (0.5% final concentration). Table 5 shows the results Table 5
Effect of compounds on clotting activity of thrombin

| Compound No. | Final concentration (M) | Percent Inhibition of clotting activity (%) | Compound No. | Final concentration (M) | Percent Inhibition of clotting activity (%) |
|---|---|---|---|---|---|
| Control (H2O) | | 0 | Control (DMSO) | | 0 |
| | $10^{-5}$ | 13.3 | | $10^{-5}$ | −5.0 |
| | $3 \times 10^{-5}$ | 11.1 | | $3 \times 10^{-5}$ | −3.0 |
| 134 | $10^{-4}$ | 42.2 | 142 | $10^{-4}$ | 0.0 |
| | $3 \times 10^{-4}$ | 97.8 | | $3 \times 10^{-4}$ | 13.0 |
| | $10^{-3}$ | 100 | | $10^{-3}$ | 61.0 |
| | $10^{-5}$ | −2.2 | | $10^{-5}$ | −3.6 |
| | $3 \times 10^{-5}$ | 20.0 | | $3 \times 10^{-5}$ | 1.7 |
| 148 | $10^{-4}$ | 6.7 | 144 | $10^{-4}$ | 58.0 |
| | $3 \times 10^{-4}$ | 55.6 | | $3 \times 10^{-4}$ | 57.3 |
| | $10^{-3}$ | 100 | | $10^{-3}$ | 98.1 |

Table 5-continued
Effect of compounds on clotting activity of thrombin

| Compound No. | Final concentration (M) | Percent Inhibition of clotting activity (%) | Compound No. | Final concentration (M) | Percent Inhibition of clotting activity (%) |
|---|---|---|---|---|---|
| | $10^{-5}$ | −5.0 | | $10^{-5}$ | −11.7 |
| | $3 \times 10^{-5}$ | 10.0 | | $3 \times 10^{-5}$ | −9.5 |
| 137 | $10^{-4}$ | 2.0 | APPA-Na | $10^{-4}$ | 44.2 |
| | $3 \times 10^{-4}$ | 14.0 | | $3 \times 10^{-4}$ | 86.5 |
| | $10^{-3}$ | 98.0 | | $10^{-3}$ | 100.0 |

Note: APPA-Na means sodium p-amidinophenyl pyruvate.

(C) Inhibitory Activity on Thrombus Formation

White male mice (ddY strain), 4 weeks age and weighing 18–27 g, were used throughout the experiments. The antithrombin effect of compounds in vivo was demonstrated by preventing thrombus formation induced by the intravenous injection of thrombin. The intravenous injection of 300 NIH units/kg of thrombin over 30 seconds into mice was lethal to all animals. The compounds were intraperitoneally administered in doses of 1, 10, and 100 mg/kg in saline unless otherwise described.

Table 6 shows the results.

(D) The acute toxicities (LD$_{50}$) of compounds Nos. 111, 118, 144 and 148 by intraperitoneal administration in mice were 333 mg/kg, 192 mg/kg, 192 mg/kg and 92 mg/kg, respectively.

Table 6
Effects of compound Nos. 91, 118, 134, 138 and 148 and APPA-Na on lethal thrombin injection in mice.

| Compound No. | Dose mg/kg i.p. | Survived Tested | % protective |
|---|---|---|---|
| Control | — | 0/30 | 0 |
| 91 | 1 | 0/10 | 0 |
| | 10 | 0/10 | 0 |
| | 100 | 2/10 | 20 |
| 118 | 1 | 2/10 | 20 |
| | 10 | 3/10 | 30 |
| | 100 | 4/10 | 40 |
| 134 | 1 | 0/9 | 0 |
| | 10 | 1/10 | 10 |
| | 100 | 7/10 | 70 |
| 138 | 1 | 0/10 | 0 |
| | 10 | 2/10 | 20 |
| | 100 | 3/10 | 30 |
| 148 | 1 | 0/10 | 0 |
| | 10 | 3/10 | 30 |
| | 100 | 9/10 | 90 |
| APPA-Na | 1 | 0/9 | 0 |
| (Reference) | 10 | 3/9 | 33 |
| | 100 | 5/11 | 46 |

Compounds were intraperitoneally administered 10 minutes before thrombin injection. Compound No. 91 was dissolved in 2.5% gum arabic.
APPA-Na: sodium p-amidinophenyl pyruvate.

What is claimed is:

1. An amino- or guanidino-1,2,3,4-tetrahydro-1-naphthoic ester represented by the formula,

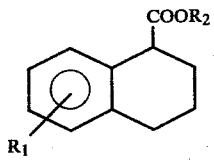

wherein $R_1$ is —NH$_2$ or

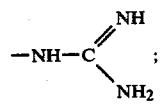

$R_2$ is

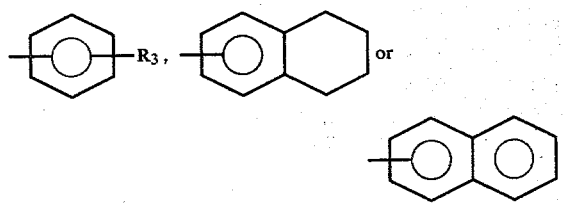

$R_3$ is —H, —R$_4$, —O—R$_4$, —COOH, —COOR$_4$,

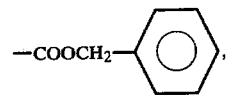

—NHCOCH$_3$, a halogen, —CN,

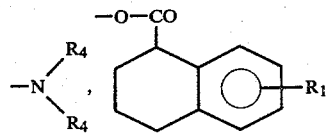

or —(CH$_2$)$_n$—COOCH$_2$—CO—R$_5$; R$_4$ is a lower alkyl group; R$_5$ is —O—R$_4$, —NH$_2$ or

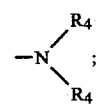

and n is 0, 1 or 2; or a pharmaceutically acceptable acid addition salt of said ester.

2. An ester or an acid addition salt thereof according to claim 1, wherein R$_2$ is phenyl group, p-, m- or o-methylphenyl group, p-, m- or o-ethylphenyl group, p-, m- or-n-propylphenyl group, p-, m- or o-n-butylphenyl group, p-, m- o-methoxyphenyl group, p-, m- or o-ethoxyphenyl group, p-, m- or o-n-propoxyphenyl group, p-, m- or o-n-butoxyphenyl group, p-, m- or o-methoxycarbonylphenyl group, p-, m- or o-ethoxycarbonylphenyl group, p-, m- or o-n-propoxycarbonylphenyl group, p-, m- or o-n-butoxycarbonylphenyl group, p-, m- or o-benzyloxycarbonylphenyl group, p-, m- or o-fluorophenyl group, p-, m- or o-chlorophenyl group, p-, m- or o-bromophenyl group, p-, m- or o-iodophenyl group, p-, m- or o-cyanophenyl group, p-, m- or o-dimethylaminophenyl group, p-, m- or o-diethylaminophenyl group, p-, m- or o-di-n-propylaminophenyl group, p-, m- or o-di-n-butylaminophenyl group, p-, m- o-acetylaminophenyl group, p-, m- or o-carboxylphenyl group, p-, m- or o-methoxycarbonylmethoxycarbonylphenyl group, p-, m- or o-ethoxycarbonylmethoxycarbonylphenyl group, p-, m- or o-n-propoxycarbonylmethoxycarbonylphenyl group, p-, m- or o-n-butoxycarbonylmethoxycarbonylphenyl group, p-, m- or o-aminocarbonylmethoxycarbonylphenyl group, p-, m- or o-dimethylaminocarbonylmethoxycarbonylphenyl group, p-, m- or o-diethylaminocarbonylmethoxycarbonylphenyl group, p-, m- or o-di-n-propylaminocarbonylmethoxycarbonylphenyl group, p-, m- or o-di-n-butylaminocarbonylmethoxycarbonylphenyl group, p-, m- or o-ethoxycarbonylmethoxycarbonylmethylphenyl group, p-, m- or o-ethoxycarbonylmethoxycarbonylethylphenyl group, p-, m- or o-dimethylaminocarbonylmethoxycarbonylmethylphenyl group, p-, m- or o-dimethylaminocarbonylmethoxycarbonylethylphenyl group, amino- or guanidino-1,2,3,4-tetrahydronaphthyl-1-carbonyloxyphenyl group, 1,2,3,4-tetrahydronaphthyl group or naphthyl group.

3. An ester or an acid addition salt thereof according to claim 1, wherein R$_2$ is phenyl group, p-, m- or o-halophenyl, p-, m- or o-methylphenyl group, p-, m- or o-ethylphenyl group, p-, m- or o-n-propylphenyl group, p-, m- or o-n-butylphenyl group, p-, m- or o-methoxyphenyl group, p-, m- or o-ethoxyphenyl group, p-, m- or o-n-propoxyphenyl group, p-, m- or o-n-butoxyphenyl group, p-, m- or o-methoxycarbonylphenyl group, p-, m- or o-ethoxycarbonylphenyl group, p-, m- or o-n-propoxycarbonylphenyl group, p-, m- or o-n-butoxycarbonylphenyl group or naphthyl group.

4. An amino-1,2,3,4-tetrahydro-1-naphthoic ester or an acid addition salt thereof according to claim 1, 2 or 3, wherein $R_1$ is $-NH_2$.

5. An amino-1,2,3,4-tetrahydro-1-naphthoic ester or an acid addition salt thereof according to claim 4, which is selected from the group consisting of p-ethoxycarbonylphenyl 5-amino-1,2,3,4-tetrahydro-1-naphthoate, phenyl 5-amino-1,2,3,4-tetrahydro-1-naphthoate, p-methoxyphenyl 5-amino-1,2,3,4-tetrahydro-1-naphthoate, naphthyl 5-amino-1,2,3,4-tetrahydro-1-naphthoate, p-methylphenyl 5-amino-1,2,3,4-tetrahydro-1-naphthoate, p-chlorophenyl 5-amino-1,2,3,4-tetrahydro-1-naphthoate, p-n-butoxyphenyl 5-amino-1,2,3,4-tetrahydro-1-naphthoate, phenyl 7-amino-1,2,3,4-tetrahydro-1-naphthoate, p-ethoxycarbonylphenyl 7-amino-1,2,3,4-tetrahydro-1-naphthoate, p-methoxyphenyl 7-amino-1,2,3,4-tetrahydro-1-naphthoate, naphthyl 7-amino-1,2,3,4-tetrahydro-1-naphthoate, p-methylphenyl 7-amino-1,2,3,4-tetrahydro-1-naphthoate, p-chlorophenyl 7-amino-1,2,3,4-tetrahydro-1-naphthoate, p-n-butoxyphenyl 7-amino-1,2,3,4-tetrahydro-1-naphthoate, and hydrochlorides and carbonates of these esters.

6. An acid addition salt of an amino-1,2,3,4-tetrahydro-1-naphthoic ester according to claim 4, which is selected from the group consisting of p-methoxycarbonylphenyl 5-amino-1,2,3,4-tetrahydro-1-naphthoate hydrochloride, p-ethoxycarbonylphenyl 5-amino-1,2,3,4-tetrahydro-1-naphthoate hydrochloride and p-chlorophenyl 7-amino-1,2,3,4-tetrahydro-1-naphthoate hydrochloride.

7. A guanidino-1,2,3,4-tetrahydro-1-naphthoic ester or an acid addition salt thereof according to claim 1, 2 or 3, wherein $R_1$ is

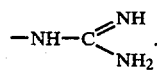

8. A guanidino-1,2,3,4-tetrahydro-1-naphthoic ester or an acid addition salt thereof according to claim 7, which is selected from the group consisting of phenyl 5-guanidino-1,2,3,4-tetrahydro-1-naphthoate, p-ethoxycarbonylphenyl 5-guanidino-1,2,3,4-tetrahydro-1-naphthoate, p-methoxyphenyl 5-guanidino-1,2,3,4-tetrahydro-1-naphthoate, naphthyl 5-guanidino-1,2,3,4-tetrahydro-1-naphthoate, p-methylphenyl 5-guanidino-1,2,3,4-tetrahydro-1-naphthoate, p-chlorophenyl 5-guanidino-1,2,3,4-tetrahydro-1-naphthoate, p-n-butoxyphenyl 5-guanidino-1,2,3,4-tetrahydro-1-naphthoate, phenyl 7-guanidino-1,2,3,4-tetrahydro-1-naphthoate, p-ethoxycarbonylphenyl 7-guanidino-1,2,3,4-tetrahydro-1-naphthoate, p-methoxyphenyl 7-guanidino-1,2,3,4-tetrahydro-1-naphthoate, naphthyl 7-guanidino-1,2,3,4-tetrahydro-1-naphthoate, p-methylphenyl 7-guanidino-1,2,3,4-tetrahydro-1-naphthoate, p-chlorophenyl 7-guanidino-1,2,3,4-tetrahydro-1-naphthoate, p-n-butoxyphenyl 7-guanidino-1,2,3,4-tetrahydro-1-naphthoate, and hydrochlorides and carbonates of these esters.

9. An acid addition salt of a guanidino-1,2,3,4-tetrahydro-1-naphthoic ester according to claim 7, which is selected from the group consisting of p-methoxycarbonylphenyl 5-guanidino-1,2,3,4-tetrahydro-1-naphthoate hydrochloride, p-chlorophenyl 5-guanidino-1,2,3,4-tetrahydro-1-naphthoate hydrochloride, phenyl 7-guanidino-1,2,3,4-tetrahydro-1-naphthoate hydrochloride, p-methoxyphenyl 7-guanidino-1,2,3,4-tetrahydro-1-naphthoate hydrochloride, p-methoxycarbonylphenyl 7-guanidino-1,2,3,4-tetrahydro-1-naphthoate hydrochloride, and p-ethoxycarbonylphenyl 7-guanidino-1,2,3,4-tetrahydro-1-naphthoate hydrochloride.

10. An amino- or guanidino-1,2,3,4-tetrahydro-1-naphthoic ester or an acid addition salt thereof according to claim 1, wherein $R_2$ is $-(CH_2)_n-COOCH_2-CO-R_5$, where $R_5$ is $-O-R_4$, $-NH_2$ or

n is 0, 1 or 2; and $R_4$ is a lower alkyl group.

11. An amino- or guanidino-1,2,3,4-tetrahydro-1-naphthoic ester or an acid addition salt thereof according to claim 10, wherein $R_2$ is p-, m- or o-methoxycarbonylmethoxycarbonylphenyl, p-, m- or o-ethoxycarbonylmethoxycarbonylphenyl, p-, m- or o-n-propoxycarbonylmethoxycarbonylphenyl, p-, m- or o-n-butoxycarbonylmethoxycarbonylphenyl, p-, m- or o-aminocarbonylmethoxycarbonylphenyl, p-, m- or o-dimethylaminocarbonylmethoxycarbonylphenyl, p-, m- or o-diethylaminocarbonylmethoxycarbonylphenyl, p-, m- or o-di-n-propylaminocarbonylmethoxycarbonylphenyl, p-, m- or o-di-n-butylaminocarbonylmethoxycarbonylphenyl, p-, m- or o-ethoxycarbonylmethoxycarbonylmethylphenyl, p-, m- or o-ethoxycarbonylmethoxycarbonylethylphenyl, p-, m- or o-dimethylaminocarbonylmethoxycarbonylmethylphenyl, or p-, m- or o-dimethylaminocarbonylmethoxycarbonylethylphenyl.

12. An amino- or guanidino-1,2,3,4-tetrahydro-1-naphthoic ester or an acid addition salt thereof according to claim 10, which is selected from the group consisting of p-ethoxycarbonylmethoxycarbonylphenyl 5-amino-1,2,3,4-tetrahydro-1-naphthoate, p-aminocarbonylmethoxycarbonylphenyl 5-amino-1,2,3,4-tetrahydro-1-naphthoate, p-dimethylaminocarbonylmethoxycarbonylphenyl 5-amino-1,2,3,4-tetrahydro-1-naphthoate, p-dimethylaminocarbonylmethoxycarbonylmethylphenyl 5-amino-1,2,3,4-tetrahydro-1-naphthoate, p-ethoxycarbonylmethoxycarbonylethylphenyl 5-amino-1,2,3,4-tetrahydro-1-naphthoate, p-dimethylaminocarbonylmethoxycarbonylethylphenyl 5-amino-1,2,3,4-tetrahydro-1-naphthoate, p-ethoxycarbonylmethoxycarbonylphenyl 7-amino-1,2,3,4-tetrahydro-1-naphthoate, p-aminocarbonylmethoxycarbonylphenyl 7-amino-1,2,3,4-tetrahydro-1-naphthoate, p-dimethylaminocarbonylmethoxycarbonylphenyl 7-amino-1,2,3,4-tetrahydro-1-naphthoate, p-dimethylaminocarbonylmethoxycarbonylmethylphenyl 7-amino-1,2,3,4-tetrahydro-1-naphthoate, p-ethoxycarbonylmethoxycarbonylethylphenyl 7-amino-1,2,3,4-tetrahydro-1-naphthoate, p-dimethylaminocarbonylmethoxycarbonylethylphenyl 7-amino-1,2,3,4-tetrahydro-1-naphthoate, p-ethoxycarbonylmethoxycarbonylphenyl 5-guanidino-1,2,3,4-tetrahydro-1-naphthoate, p-aminocarbonylmethoxycarbonylphenyl 5-guanidino-1,2,3,4-tetrahydro-1-naphthoate, p-dimethylaminocarbonylmethoxycarbonylphenyl 5-guanidino-1,2,3,4-tetrahydro-1-naphthoate, p-dimethylaminocarbonylmethoxycarbonylmethylphenyl 5-guanidino-1,2,3,4-tetrahydro-1-naphthoate, p-ethoxycarbonylmethoxycarbonylethylphenyl 5-guanidino-1,2,3,4-tetrahydro-1-naphthoate, p-dimethylaminocarbonylmethoxycarbonylethylphenyl 5-guanidino-1,2,3,4-tetrahydro-1-naphthoate, p-ethoxycarbonylmethoxycarbonylphenyl 7-guanidino-1,2,3,4-tetrahydro-1-naphthoate, p-aminocarbonylmethoxycarbonylphenyl 7-guanidino-1,2,3,4-tetrahydro-1-naphthoate, p-dimetylaminocarbonylmethoxycarbonylphenyl 7-guanidino-1,2,3,4-tetrahydro-1-naphthoate, p-dimethylaminocarbonylmethoxycarbonylmethylphenyl 7-guanidino-1,2,3,4-tetrahydro-1-naphthoate, p-ethoxycarbonylmethoxycarbonylethylphenyl 7-guanidino-1,2,3,4-tetrahydro-1-naphthoate, p-dimethylaminocarbonylmethoxycarbonylethylphenyl 7-guanidino-1,2,3,4-tetrahydro-1-naphthoate, and hydrochlorides and carbonates of these esters.

* * * * *